US00PP34661P2

(12) United States Plant Patent
Sidhu

(10) Patent No.: US PP34,661 P2
(45) Date of Patent: Oct. 18, 2022

(54) ***GAULTHERIA* PLANT NAMED 'GAULSIDH4'**

(50) Latin Name: *Gaultheria shallon*
Varietal Denomination: 'Gaulsidh4'

(71) Applicant: Gurjit Sidhu, Mission (CA)

(72) Inventor: Gurjit Sidhu, Mission (CA)

( * ) Notice: Subject to any disclaimer, the term of this patent is extended or adjusted under 35 U.S.C. 154(b) by 0 days.

(21) Appl. No.: 17/701,023

(22) Filed: Mar. 22, 2022

(30) Foreign Application Priority Data

Apr. 15, 2021 (CA) ..... 21-10462

(51) Int. Cl.
*A01H 5/00* (2018.01)
*A01H 6/36* (2018.01)

(52) U.S. Cl.
USPC ..... Plt./226
CPC ..... *A01H 6/36* (2018.05)

(58) Field of Classification Search
USPC ..... Plt./226
CPC ..... A01H 5/02; A01H 5/00
See application file for complete search history.

*Primary Examiner* — Kent L Bell
(74) *Attorney, Agent, or Firm* — Penny J. Aguirre

(57) ABSTRACT

A new cultivar of *Gautheria shallon* plant named 'Gaulsidh4' that is characterized by its leaves that are small in size and ovate to round in shape, its very compact plant habit, and its floriferous blooming habit.

2 Drawing Sheets

Botanical classification: *Gaultheria shallon.*
Cultivar designation: 'Gaulsidh4'.

CROSS REFERENCE TO RELATED APPLICATIONS

This application claims priority to a Canadian Plant Breeder's Rights Application No. 21-10462 filed on Apr. 15, 2021, under 35 U.S.C. 119(f), the entire contents of which is incorporated by reference herein. This application is also co-pending with a U.S. Plant Patent Application filed for a plant derived from the same breeding program that is entitled *Gaultheria* Plant Named 'Gaulsidh12' (U.S. Plant patent application Ser. No. 17/701,052).

BACKGROUND OF THE INVENTION

The present invention relates to a new and distinct cultivar of *Gaultheria shallon*, botanically known as *Gaultheria shallon* 'Gaulsidh4' and is hereinafter referred to by its cultivar name 'Gaulsidh4'.

'Gaulsidh4' was discovered by the Inventor as a chance seedling that was growing in a container in Mission, B.C., Canada in spring of 2014. The containers had been planted with seed derived from unnamed and unpatented plants of *Gaultheria shallon*. The exact parents are unknown.

Asexual propagation of the new cultivar was first accomplished by tissue culture using meristemac tissue under the direction of the Inventor in Mission, B.C., Canada in spring of 2015. Asexual propagation of the new cultivar by tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Gaulsidh4' as a new and unique cultivar of *Gaultheria.*

1. 'Gaulsidh4' exhibits leaves that are small in size and ovate to round in shape.
2. 'Gaulsidh4' exhibits a very compact plant habit.
3. 'Gaulsidh4' exhibits a floriferous blooming habit.

'Gaulsidh4' can be most closely compared to a typical unnamed plant of *Gaultheria shallon* and 'Gaulsidh12'. Both are similar to 'Gaulsidh4' in flower color. The unnamed *Gaultheria shallon* differs from 'Gaulsidh4' in having a much larger plant size and in being less floriferous. 'Gaulsidh12' differs from 'Gaulsidh4' in having a larger plant size, a less compact plant size, new growth that is red in color, leaves that are more narrow and pointed in shape, and in being less floriferous.

BRIEF DESCRIPTION OF THE DRAWINGS

The accompanying color photographs illustrate the overall appearance and distinct characteristics of two year-old plants as grown outdoors in 1-gallon containers in St. Thomas, Ontario, Canada.

The photograph in FIG. 1 provides a side view of the plant habit of 'Gaulsidh4'.

Figure 1:
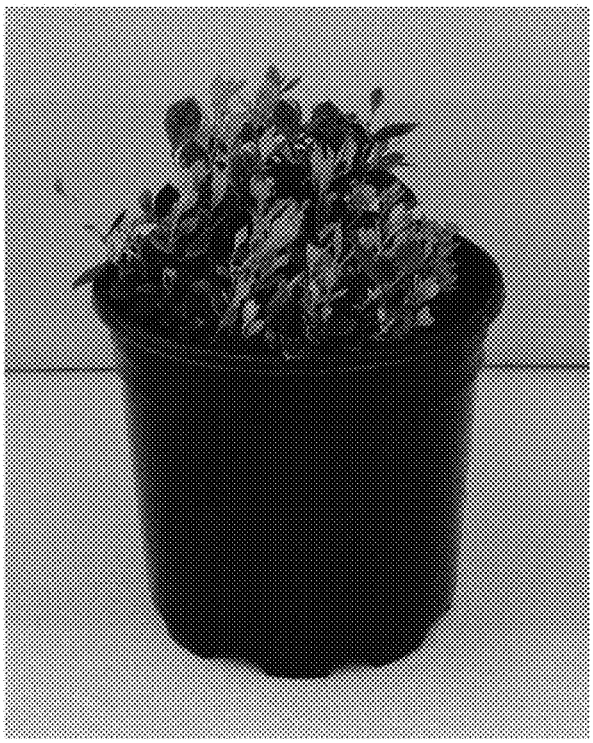
Figure 2:
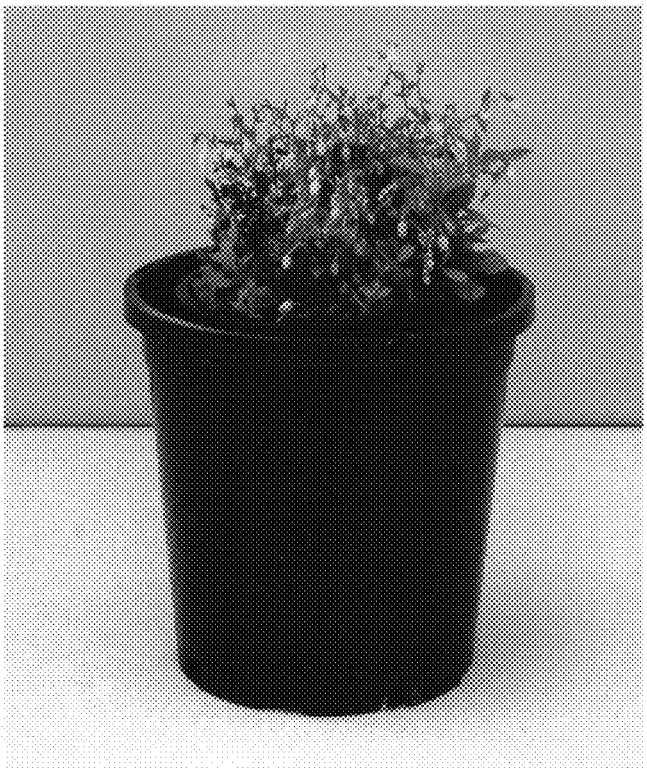

The photograph in FIG. 2 provides a side view of 'Gaulsidh4' in bloom.

Figure 3:
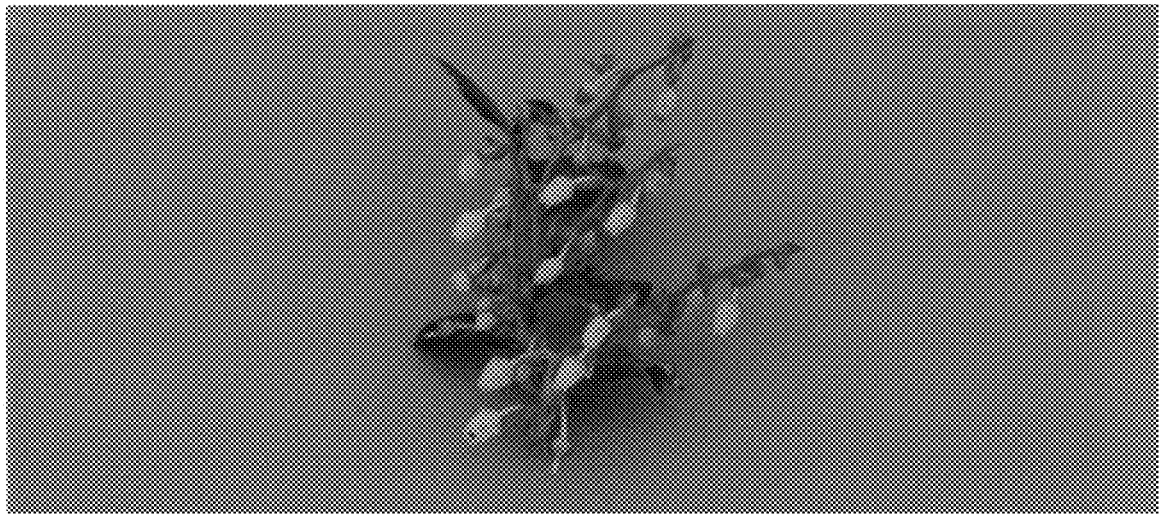

The photograph in FIG. 3 provides a close-up view of the flowers of 'Gaulsidh4'.

Figure 4:
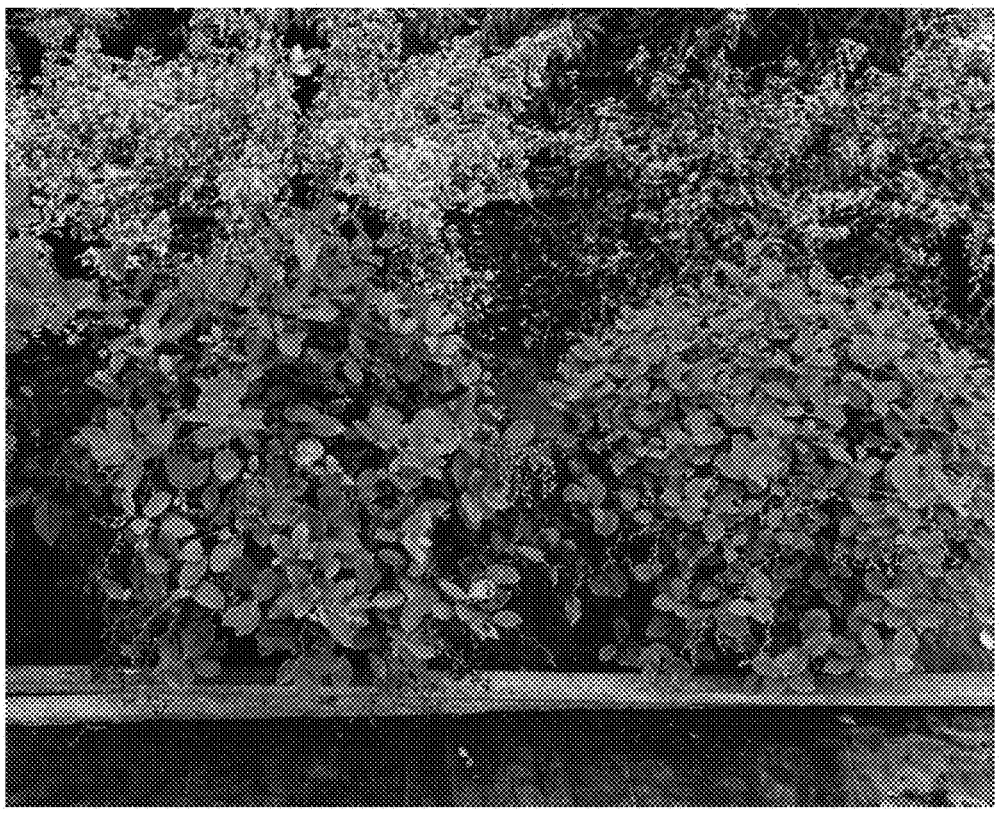

The photograph in FIG. 4 provides a comparison view between 'Gaulsidh12' (left) and 'Gaulsidh4' (right).

The colors in the photographs may differ slightly from the color values cited in the detailed botanical description, which accurately describe the colors of the new *Gaultheria.*

DETAILED BOTANICAL DESCRIPTION OF THE PLANT

The following is a detailed description of 2.5-year-old plants of the new cultivar grown outdoors in 1-gallon containers in St. Thomas, Ontario, Canada. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Four to six weeks from late spring to late summer in Ontario, Canada.

*Plant type.*—Evergreen shrub.

*Plant habit.*—Compact.

*Plant shape.*—Oblate.

*Height and spread.*—Reaching an average of 14.6 cm in height, 24.8 cm in width as a 2.5 year-old plant in a one-gallon container, 45 cm in height, 60 cm in width in the landscape.

*Cold hardiness.*—At least in U.S.D.A. Zone 6.

*Diseases and pests.*—No resistance or susceptibility to diseases or pests has been observed.

*Propagation.*—Tissue culture.

*Root development.*—2 to 3 weeks to initiate roots in tissue culture, an average of 12 months to fully root in a liner.

*Growth rate and vigor.*—Low.

Stem description:

*Shape.*—Round.

*Stem color.*—New stem; 181A, and may be 145C on non-sunny side, mature; 145C.

*Stem size.*—An average of 16.6 cm in length and 1.0 mm in width.

*Stem surface.*—Smooth and pubescent.

*Stem strength.*—Medium.

*Branching.*—Freely branching, an average of 10 basal branches each with approximately 3 secondary branches, further divided to approximately 12 new stems.

*Branch angle.*—Upright.

*Branch internode length.*—Up to 5.8 mm.

Foliage description:

*Leaf shape.*—Ovate to round.

*Leaf division.*—Simple.

*Leaf base.*—Cuneate to rounded.

*Leaf apex.*—Acute to cuspidate.

*Leaf fragrance.*—Wintergreen if crushed.

*Leaf venation.*—Pinnate, young leaf color; mid vein of upper surface 145C, mid vein of lower surface 145C, mature leaf color; mid vein of upper surface 1D, mid vein of lower surface; 145C.

*Leaf margins.*—Irregularly serrate, single small hair emerging from the tip of each tooth, up to 1 mm in length and 166A in color.

*Leaf arrangement.*—Alternate and clustered near tips.

*Leaf attachment.*—Petiolate.

*Leaf number.*—Average of 10 per branch.

*Leaf surface.*—Upper and lower surface; smooth, glabrous, moderately glossy and leathery.

*Leaf variegation.*—Absent.

*Leaf size.*—Average of 3.9 cm in length and 2.7 cm in width.

*Leaf color.*—Young leaves upper surface; 144B, margins 180C and 181C, young leaves lower surface; 144D, mature leaves upper surface; 147A, mature leaves lower surface; 147B.

*Petioles.*—Average of 2.9 mm in length, upper and lower surfaces are dull, color of upper surface; 145B, color of lower surface; 145C.

Inflorescence description:

*Inflorescence.*—Axillary and terminal clusters of individual flowers.

*Inflorescence size.*—Average of 6.8 cm in length.

*Lastingness of inflorescence.*—Average of 2 weeks, self cleaning (sepals and petals).

*Number of flowers.*—4 to 7 per flowering branch, average of 170 per plant.

*Flower buds.*—Ovate in shape, average of 6 mm in length and 4 mm in width, color NN155B suffused with 58C towards base, satiny surface.

*Flower size.*—Average of 8 mm in length and 7 mm in width.

*Corolla.*—Urceolate in shape, comprised of 5 fused ovate shaped petals with rounded tips (5%) free that are moderately reflexed, free parts are 1 mm in length and 1 mm width, width of aperture 4 mm, color NN155D with 67D towards apex, when opening and mature, both surfaces are satiny and glabrous and very slightly ribbed on inner and outer surfaces.

*Calyx.*—Rotate in arrangement, average of 5 mm in depth and 7 mm in diameter.

*Sepals.*—5, ovate in shape with base fused (lower 25% fused into ring), average of about 4 mm in length and 2 mm in width, acute apex, color 155B with 145D towards base, dull on both surfaces, moderately strigose pubescence about 1 mm in length and 185A in color.

*Bracts.*—2 small bracts, an average of 1 mm in length and width, ovate in shape, truncate base, acute apex, glossy on both surfaces, color 155B suffused with 62B.

*Peduncles.*—Round, curved to hang downward, an average of 2 mm in length and 1 mm in width, 185B in color, pubescent surface.

*Pedicels.*—None, peduncles arise directly from stem node.

Reproductive organs:

*Androecium.*—Stamens; average of 10, anthers; dorsifixed, narrow deltoid in shape, 60B in color and 2 mm in length, filaments; oblong in shape, 4 mm in length, 1 mm in width and 145D in color, highly pubescent, pollen; moderate in quantity and NN155C in color.

*Gynoecium.*—Pistil; 1, stigma; club-shaped, 1 mm in length and width, 145D in color, style; average of 6 mm in length, 157D in color, ovary; round in shape, 6-parted, 2.5 mm in diameter and depth, 145C in color.

Fruit description:

*Type.*—Berry.

*Number.*—Average of 3 to 7 per lateral branch.

*Fruit size.*—Up to 8.1 mm in length and 7.5 mm in width.

*Fruit skin color.*—Young fruit; 183A, mature fruit; 202A.

*Fruit flesh.*—155B in color, glistening and spongy in texture.

*Fruit surface.*—Slightly glossy and glabrous.

*Fruit shape.*—Oblate with indented apex and 5 bluntly acute extended tips, tip size is 5 mm in length and 6 mm in width, persistent style, 5 mm in length.

*Seeds.*—Approximately 28 cylindrical shaped seeds, glossy surface, less than 1 mm in length and width, 160D in color.

It is claimed:

1. A new and distinct cultivar of *Gaultheria* plant named 'Gaulsidh4' as herein illustrated and described.

* * * * *